United States Patent
Sakai et al.

(10) Patent No.: US 10,524,646 B2
(45) Date of Patent: Jan. 7, 2020

(54) LIGHT SOURCE APPARATUS

(71) Applicant: OLYMPUS CORPORATION, Tokyo (JP)

(72) Inventors: Aiko Sakai, Kodaira (JP); Yusuke Yabe, Chofu (JP); Tomoya Takahashi, Hachioji (JP); Kazue Hongo, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/478,328

(22) Filed: Apr. 4, 2017

(65) Prior Publication Data
US 2017/0202445 A1    Jul. 20, 2017

Related U.S. Application Data
(63) Continuation of application No. PCT/JP2015/078021, filed on Oct. 2, 2015.

(30) Foreign Application Priority Data
Oct. 10, 2014    (JP) .................. 2014-209229

(51) Int. Cl.
*A61B 1/06*    (2006.01)
*G02B 23/24*   (2006.01)
(Continued)

(52) U.S. Cl.
CPC ........ *A61B 1/0684* (2013.01); *A61B 1/00009* (2013.01); *A61B 1/00045* (2013.01);
(Continued)

(58) Field of Classification Search
CPC ... A61B 1/0684; A61B 1/00045; A61B 1/051; A61B 1/0676; A61B 1/00009;
(Continued)

(56) References Cited

U.S. PATENT DOCUMENTS 5,584,557 A * 12/1996 Alexay .................. G01N 21/05
362/302
2006/0173353 A1    8/2006 Uchida
(Continued)

FOREIGN PATENT DOCUMENTS

CN    1963627 A    5/2007
CN    102355769 A    2/2012
(Continued)

OTHER PUBLICATIONS

International Search Report dated Dec. 15, 2015 issued in PCT/JP2015/078021.
(Continued)

Primary Examiner — Alexandra L Newton
Assistant Examiner — Genja M Frankert
(74) Attorney, Agent, or Firm — Scully, Scott, Murphy & Presser, P.C.

(57) ABSTRACT

A light source apparatus includes: a light source; a light source driving section; a light detection section; a temperature detection section; and a control section being configured to, when determining that detected brightness is outside a range of brightness set for detecting abnormality in the light source or the light detection section and detected temperature is within a range of temperature set for detecting the abnormality in the light source or the light detection section, cause the light source driving section to perform driving of the light source for a case of abnormality in the light detection section, and when determining that the detected brightness is outside the range of brightness and the detected temperature is outside the range of temperature, cause the light source driving section to perform driving of the light source for a case of abnormality in the light source.

7 Claims, 8 Drawing Sheets

(51) Int. Cl.
*A61B 1/00* (2006.01)
*A61B 1/05* (2006.01)
*H05B 33/08* (2006.01)
*H04N 5/225* (2006.01)
*H04N 5/235* (2006.01)

(52) U.S. Cl.
CPC ............ *A61B 1/051* (2013.01); *A61B 1/0676* (2013.01); *G02B 23/2469* (2013.01); *H05B 33/089* (2013.01); *H05B 33/0869* (2013.01); *H05B 33/0872* (2013.01); *H04N 5/2256* (2013.01); *H04N 5/2354* (2013.01); *H04N 2005/2255* (2013.01)

(58) Field of Classification Search
CPC .... A61B 1/06; H05B 33/0884; H05B 33/089; H05B 33/0866; H05B 33/0872; H05B 33/0869; H04N 2005/2255; H04N 5/2256; H04N 5/2354; G02B 23/2469; G02B 23/26
See application file for complete search history.

(56) References Cited

U.S. PATENT DOCUMENTS

| | | |
|---|---|---|
| 2013/0162692 A1 | 6/2013 | Wang |
| 2013/0181612 A1 | 7/2013 | Ohno |
| 2014/0049624 A1 | 2/2014 | Masaki et al. |
| 2014/0054450 A1 | 2/2014 | Shirota et al. |
| 2016/0343757 A1* | 11/2016 | Enichlmair ....... H01L 27/14625 |

FOREIGN PATENT DOCUMENTS

| | | |
|---|---|---|
| CN | 103185636 A | 7/2013 |
| CN | 103218979 A | 7/2013 |
| CN | 203608439 U | 5/2014 |
| EP | 1754443 A1 | 2/2007 |
| EP | 2702928 A1 | 3/2014 |
| EP | 2737843 A1 | 6/2014 |
| JP | S61-274379 A | 12/1986 |
| JP | H11-313797 A | 11/1999 |
| JP | 2005-204910 A | 8/2005 |
| JP | 2005-348912 A | 12/2005 |
| JP | 2006-186054 A | 7/2006 |
| JP | 2009-043784 A | 2/2009 |
| JP | 2012-119141 A | 6/2012 |
| JP | 5393935 B1 | 1/2014 |
| JP | 5467181 B1 | 4/2014 |
| WO | WO 2005/120361 A1 | 12/2005 |
| WO | WO 2013/146014 A1 | 10/2013 |
| WO | WO 2013/150897 A1 | 10/2013 |

OTHER PUBLICATIONS

Japanese Office Action dated Jul. 19, 2016 issued in JP 2016-524611.
Extended Supplementary European Search Report dated Apr. 5, 2018 in European Patent Application No. 15 84 8912.0.

* cited by examiner

| DRIVING CURRENT[A] | MINIMUM ILLUMINANCE[lx] | MAXIMUM ILLUMINANCE[lx] |
|---|---|---|
| 1 | A1 | A2 |
| 2 | B1 | B2 |
| 3 | C1 | C2 |
| 4 | D1 | D2 |
| 5 | E1 | E2 |

41b

| DRIVING CURRENT[A] | MINIMUM TEMPERATURE[°C] | MAXIMUM TEMPERATURE[°C] |
|---|---|---|
| 1 | A3 | A4 |
| 2 | B3 | B4 |
| 3 | C3 | C4 |
| 4 | D3 | D4 |
| 5 | E3 | E4 |

*41d*

LIGHT SOURCE APPARATUS

CROSS REFERENCE TO RELATED APPLICATION

This application is a continuation application of PCT/JP2015/078021 filed on Oct. 2, 2015 and claims benefit of Japanese Application No. 2014-209229 filed in Japan on Oct. 10, 2014, the entire contents of which are incorporated herein by this reference.

BACKGROUND OF THE INVENTION

1. Field of the Invention

The present invention relates to a light source apparatus preferable for an endoscope.

2. Description of the Related Art

Conventionally, endoscopes have been widely used, and such endoscopes are configured to observe a region to be examined and conduct various treatments by inserting an elongated endoscope into a body cavity or the like. In such endoscopes, light source apparatuses are used to perform photographing inside the body cavity. In recent years, light source apparatuses also have been used, which adopt a semiconductor light source such as an LED as a light-emitting portion.

As an example of such a light source apparatus, Japanese Patent Application Laid-Open Publication No. 11-313797, for example, discloses a light source apparatus including a plurality of light-emitting elements. The light source apparatus includes a light detection section that detects a light quantity of illumination light from an illumination section configured by the plurality of light-emitting elements, and compares the light quantity detected by the light detection section with a predetermined light quantity, and when the light quantity detected by the light detection section is smaller than the predetermined light quantity, displays light-emitting element replacement. The conventional light source apparatus is thus capable of detecting the lifetime of the light-emitting elements from the detection result of the light detection section.

In addition, in recent years, a light source apparatus which is provided with a plurality of light detection sections for detecting the respective light quantities of the plurality of light-emitting elements and which is configured to adjust color balance based on the light quantities detected by the plurality of light detection sections has been used.

SUMMARY OF THE INVENTION

A light source apparatus according to one aspect of the present invention includes: a light source that emits light; a light source driving section that drives the light source; a light detection section that detects brightness of the light emitted from the light source; a temperature detection section that detects a temperature of the light source; and a control section that determines whether or not the brightness detected by the light detection section is within a range of brightness set for determining abnormality in the light source or the light detection section and also determines whether or not the temperature of the light source is within a range of temperature set for detecting the abnormality in the light source or the light detection section, the control section being configured to, when determining that the brightness detected by the light detection section is outside the range of brightness and the temperature detected by the temperature detection section is within the range of temperature, cause the light source driving section to perform driving of the light source for a case of abnormality in the light detection section, and when determining that the brightness detected by the light detection section is outside the range of brightness and the temperature detected by the temperature detection section is outside the range of temperature, cause the light source driving section to perform driving of the light source for a case of abnormality in the light source.

BRIEF DESCRIPTION OF THE DRAWINGS

FIG. 2A is a table for explaining an example of information stored in a memory 41a.

FIG. 2B is a graph for explaining an example of the information stored in the memory 41a.

FIG. 5A is a table for explaining an example of the information stored in the memory 41a.

FIG. 5B is a graph for explaining an example of the information stored in the memory 41a.

DETAILED DESCRIPTION OF THE PREFERRED EMBODIMENTS

Hereinafter, embodiments of the present invention will be described in detail with reference to drawings.

(First Embodiment)

Figure 1:
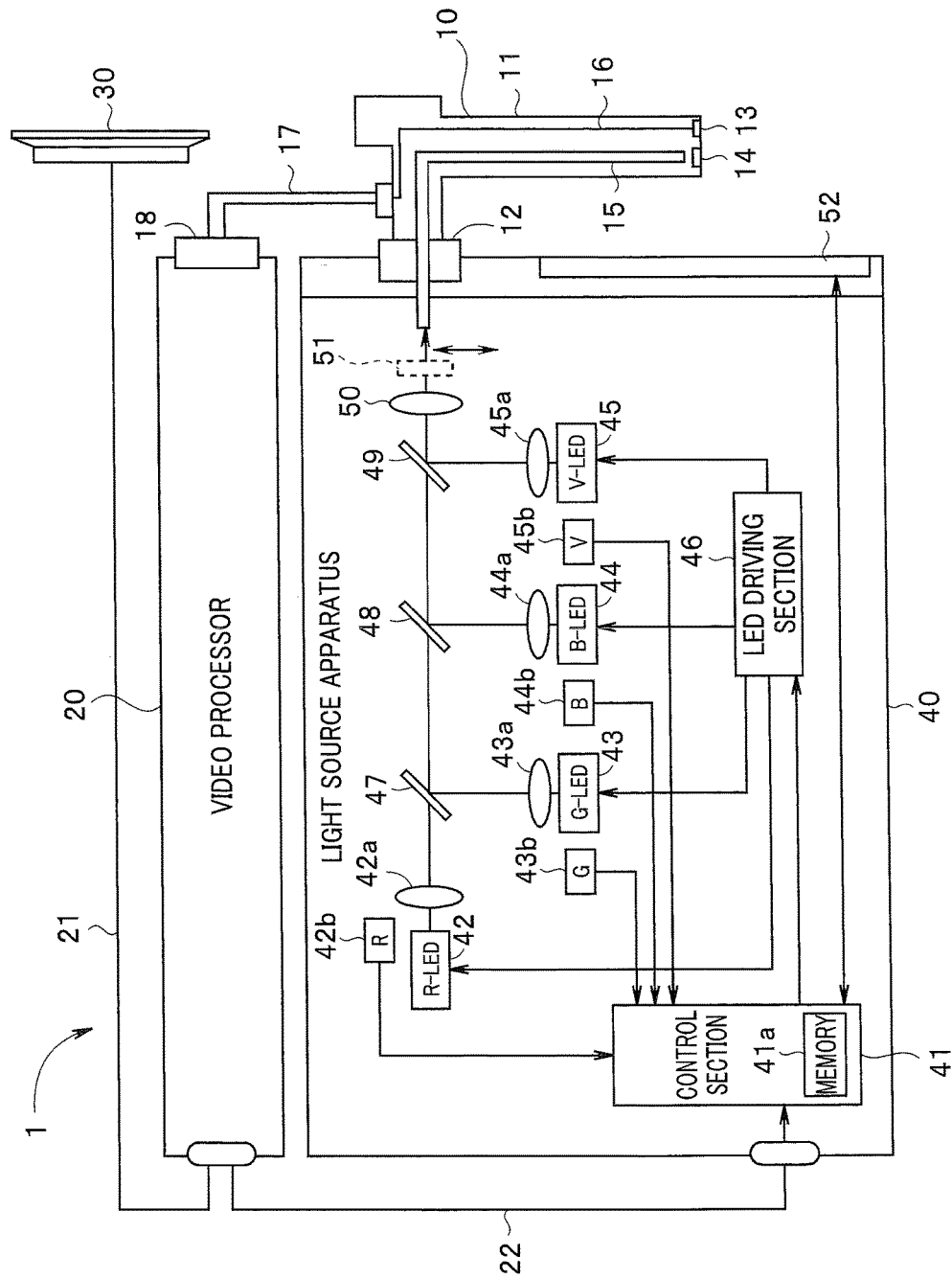
FIG. 1 a block diagram showing an endoscope system including a light source apparatus according to a first embodiment.

FIG. 1 is a block diagram showing an endoscope system including a light source apparatus according to the first embodiment. In the present embodiment, the light source apparatus is applied to the endoscope system including an endoscope, a video processor, and a monitor.

An endoscope system 1 includes an endoscope 10, a video processor 20, a monitor 30, and a light source apparatus 40. The endoscope 10 includes, on a distal end side thereof, an elongated insertion portion 11 configured to be insertable into a lumen, and a proximal end side of the endoscope 10 is configured to be detachably connected to a light source apparatus 40 through a connector 12.

In addition, the endoscope 10 is detachably connected to a video processor 20 through a cable 17 and a connector 18. Thus, different types of endoscopes can be attached to the light source apparatus 40 and the video processor 20.

The insertion portion 11 includes at a distal end thereof an image pickup device 13 for picking up a video of an object such as inside of a lumen and a lens 14 for applying light from the light source apparatus 40 to the object. The illumination light transmitted from the light source apparatus 40 through the light guide 15 is applied to the object through the lens 14. The image pickup device 13 is configured with CCD, CMOS sensor, or the like. The return light from the object is incident on an image pickup surface, and the image pickup device photoelectrically converts the incident optical image of the object and sequentially outputs image pickup signals based on accumulated electric charge.

The image pickup device 13 operates by receiving a driving signal including a synchronization signal from the video processor 20, and supplies image pickup signals to the video processor 20 through a signal line 16.

The video processor 20 performs predetermined signal processing on the image pickup signals to generate a video signal which can be displayed on a monitor 30. The video signal from the video processor 20 is supplied to the monitor 30 through a cable 21. Thus, an endoscopic image based on the image pickup signals can be displayed on the display screen of the monitor 30.

In addition, the video processor 20 is capable of controlling the light source apparatus 40 such that the brightness of the picked-up image becomes target brightness. The video processor 20 is configured to output information on a ratio of the brightness obtained from the picked-up image to the target brightness to the light source apparatus 40, as brightness control information. The brightness control information is supplied to the control section 41 of the light source apparatus 40 through a cable 22.

The light source apparatus 40 includes an LED (R-LED) 42 that generates red light, an LED (G-LED) 43 that generates green light, an LED (B-LED) 44 that generates blue light, and an LED (V-LED) 45 that generates violet light. Each of the LEDs 42 to 45, which constitute a plurality of semiconductor light-emitting elements, emits a different color of illumination light for illuminating the object. Note that description will be made on an example adopting the four LEDs that generate light beams of four colors in the present embodiment. However, the type of colors and the number of colors are not limited to those in the present embodiment. A plurality of kinds of LEDs have only to be used in the present embodiment, and an LED that generates amber light may also be added in FIG. 1, for example.

Lenses 42a to 45a are arranged respectively on optical axes of emitted light beams from the LEDs 42 to 45. The respective lenses 42a to 45a transform the emitted light beams from the LEDs 42 to 45 into substantially parallel light beams and emit the parallel light beams. Dichroic filters 47 to 49 are arranged on the optical axis of the lens 42a through which the light from the R-LED 42 is emitted. The light from the G-LED 43 is also incident on the dichroic filter 47 through the lens 43a. In addition, the light from the B-LED 44 is incident on the dichroic filter 48 through the lens 44a, and the light from the V-LED 45 is incident on the dichroic filter 49 through the lens 45a.

The dichroic filter 47 reflects the light from the G-LED 43 and transmits the light from the R-LED 42. Similarly, the dichroic filter 48 reflects the light from the B-LED 44 and transmits the light transmitted through the dichroic filter 47. Similarly, the dichroic filter 49 reflects the light from the V-LED 45 and transmits the light transmitted through the dichroic filter 48.

Thus, the light beams from the LEDs 42 to 45 are synthesized by the dichroic filters 47 to 49. The synthesized light emitted from the dichroic filter 49 enters the light guide 15 through a lens 50. Note that the arranging order of the LEDs 42 to 45 can be changed by appropriately setting the characteristics of the dichroic filters 47 to 49. However, if the LEDs 42 to 45 are arranged in the order of wavelength bands of the light beams emitted from the LEDs, it is more easy to set the characteristics of the dichroic filters.

The LEDs 42 to 45 are driven to be turned on by an LED driving section 46. The LED driving section 46 that constitutes a light-emitting element driving section is controlled by the control section 41, to generate PWM pulses as the driving signals for driving the LEDs 42 to 45. Each of the LEDs 42 to 45 emits light at a light emission quantity corresponding to the duty ratio and the current quantity of the PWM pulse from the LED driving section 46. The control section 41 outputs light control information for controlling the LEDs 42 to 45 to the LED driving section 46, to thereby control the duty ratios and current levels of the PWM pulses and perform light control on the LEDs 42 to 45.

In addition, optical sensors 42b to 45b are arranged at positions at which the emitted light beams from the LEDs 42 to 45 can be detected. The optical sensors 42b to 45b that constitute a plurality of light detection sections detect illuminance values of the respective colors of illumination light beams from LEDs 42 to 45 and output detection results to the control section 41. Note that the optical sensors 42b to 45b are arranged at positions other than the optical paths from the respective LEDs 42 to 45 to the lenses 42a to 45a.

The control section 41 generates light control information so as to allow the light emission quantities of the LEDs 42 to 45 to maintain a predetermined color balance. The color balance among the LEDs 42 to 45 has to be determined according to the spectral sensitivity characteristics of the endoscope 10.

The control section 41 controls the light quantities of the LEDs 42 to 45 while maintaining the ratio of the light emission quantities of the LEDs 42 to 45 (light quantity ratio) so that an optimal color balance can be obtained, based on the brightness control information from the video processor 20. For example, the control section 41 acquires light control information corresponding to the light quantity value of the G-LED 43 which is to be set based on the brightness control information from the video processor 20, and acquires light control information for other LEDs 42, 44, and 45 such that the ratio of the light quantities of the other LEDs 42, 44, and 45 becomes a predetermined ratio depending on the light quantity value of the G-LED 43.

That is, the control section 41 controls the light quantity value of the G-LED 43 based on the brightness control information from the video processor 20. Then, the control section 41 controls the light quantity values of the other LEDs 42, 44, and 45, based on the detection result of the optical sensor 43b of the G-LED 43 and the detection result of the optical sensors 42b, 44b, or 45b of the other LEDs 42, 44, and 45, so as to achieve a predetermined color balance (the light quantity ratio to the G-LED becomes a target ratio).

In addition, the control section 41 compares the illuminance values of the LEDs 42 to 45 detected by the optical sensors 42b to 45b with the information stored in the memory 41a. As detailed later, in the memory 41a that constitutes the storing section, a predetermined range of illuminance values of the LEDs 42 to 45 which correspond to the driving currents at the time of normal light-emitting of the LEDs 42 to 45 are stored as a table.

The control section 41 determines whether or not the detected illuminance values are within the predetermined range of the illuminance values, based on the relation between the driving currents and the illuminance values stored in the memory 41a. When determining that the detected illuminance values are within the predetermined range of the illuminance values, the control section 41 determines that the LEDs 42 to 45 and the optical sensors 42b to 45b are normal, and when determining that any of the detected illuminance values is not within the predetermined range of the illuminance values, the control section 41 determines that abnormality occurs in either the LEDs 42 to 45 or the optical sensors 42b to 45b.

Figures 2A, 2B:
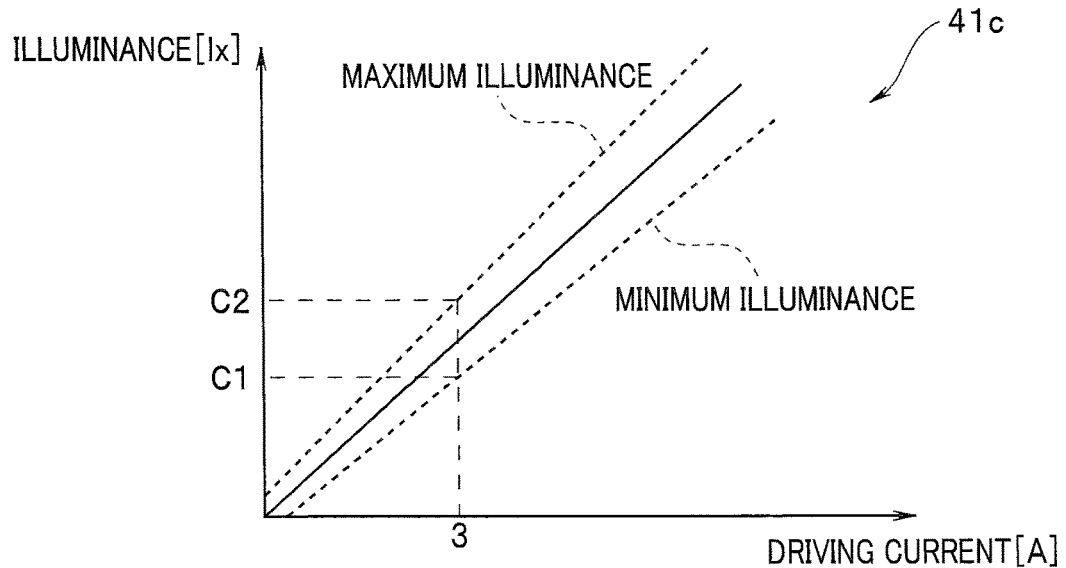

FIGS. 2A and 2B illustrate one example of the information stored in the memory 41a. In particular, FIG. 2A is a table for explaining one example of the information stored in the memory 41a, and FIG. 2B is a graph for explaining one example of the information stored in the memory 41a.

As shown in FIG. 2A, the correspondence relation among the driving currents, the minimum illuminance values, and the maximum illuminance values of the LEDs 42 to 45 is stored in the table 41b. Note that, if the relation among the driving currents, the minimum illuminance values, and the maximum illuminance values is different in each of the LEDs 42 to 45, a table for each of the LEDs 42 to 45 may be stored in the memory 41a. In addition, the minimum illuminance values and the maximum illuminance values relative to the driving currents may be obtained in advance at the time of factory shipment, for example, and stored in the memory 41a.

For example, the control section 41 refers to the table 41b, and when the illuminance value detected by each of the optical sensors 42b to 45b is within the range from the maximum illuminance C1[lx] to the maximum illuminance C2[lx] when each of the LEDs 42 to 45 is driven at the driving current 3[A], the control section 41 determines that each of the LEDs 42 to 45 and each of the optical sensors 42b to 45b are normal. When the illuminance value detected by each of the optical sensor 42b to 45b is not within the range from the minimum illuminance C1[lx] to the maximum illuminance C2[lx] when each of the LEDs 42 to 45 is driven at the driving current 3[A], the control section 41 determines that abnormality occurs in either each of the LEDs 42 to 45 or each of the optical sensors 42b to 45b.

Note that the memory 41a may store the information of the graph 41c shown in FIG. 2B, instead of the table 41b in FIG. 2A.

The control section 41 that constitutes an abnormality detection section refers to the table 41b (or the graph 41c) stored in the memory 41a, determines whether or not the illuminance values detected by the optical sensors 42b to 45b are within a predetermined range of the illuminance values. When determining that any of the detected illuminance values is not within the predetermined range of the illuminance values, the control section 41 detects abnormality in either the LEDs 42 to 45 or the optical sensors 42b to 45b.

When determining that any of the illuminance values detected by the optical sensors 42b to 45b is smaller than a predetermined illuminance value, the control section 41 stops the driving of the LED determined to be abnormal, fixes the current values of the LEDs determined to be normal, and ensures the minimum possible light emission quantity. In contrast, when determining that any of the illuminance values is larger than the predetermined illuminance value, for example, the control section 41 may stop the driving of the LED determined to be abnormal, among the LEDs 42 to 45, and fix the current values of the LEDs determined to be normal. However, when the LED driving section 46 is disabled, there is a possibility that the LEDs 42 to 45 cannot be controlled.

To address such possibility, the control section 41 may be configured to perform control of inserting a mesh member 51 for light quantity adjustment that adjusts the light quantity to a safe range, between the lens 50 and the light guide 15, when determining that any of the illuminance values detected by the optical sensors 42b to 45b is larger than the predetermined illuminance value. The mesh member 51 is insertable into and removable from a position between the lens 50 and the light guide 15 under the control of the control section 41.

Note that the member to be inserted when the light quantity is large is not limited to the mesh member 51, and an NBI filter to be used in narrow-band observation may be inserted, for example. Since a common light source apparatus is provided with an NBI filter for narrow-band observation, it is not necessary to additionally provide the mesh member 51 for light quantity adjustment.

As described above, the light source apparatus 40 is provided with the optical sensors 42b to 45b that respectively detect the illuminance values of the LEDs 42 to 45, and configured to compare the illuminance values of the LEDs 42 to 45 detected by the optical sensors 42b to 45b with the illuminance values in the table 41b stored in the memory 41a, to detect the abnormality in either the optical sensors 42b to 45b or the LEDs 42 to 45.

Therefore, the light source apparatus according to the present embodiment is capable of easily detecting abnormality in the light detection section or the light-emitting element.

(Modified Example)

Next, a modified example of the first embodiment will be described.

Figure 3:
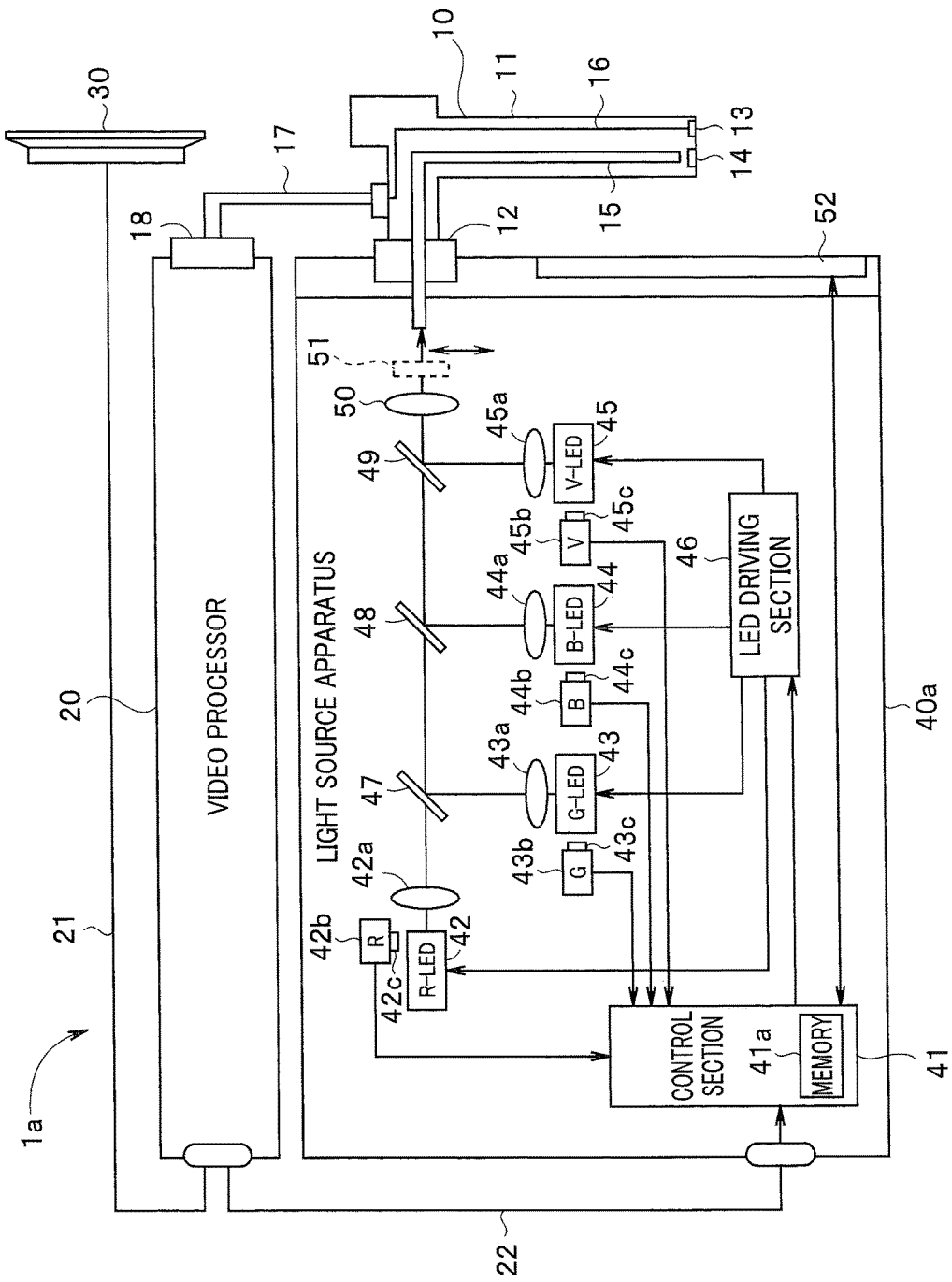
FIG. 3 is a block diagram showing a configuration of the endoscope system including a light source apparatus according to a modified example of the first embodiment.

FIG. 3 is a block diagram showing a configuration of an endoscope system including a light source apparatus according to a modified example of the first embodiment. Note that, in FIG. 3, the same constituent elements as those in FIG. 1 are attached with the same reference numerals and descriptions thereof will be omitted.

The light emission quantities of the LEDs arranged in the light source apparatus are normally large, and an LED that emits light exceeding the light-receiving limit of a common optical sensor exists. Therefore, in some cases, the light emission quantity of such an LED cannot be accurately detected with an optical sensor.

In order to address such a circumstance, a light source apparatus 40a according to the modified example includes dimmer filters 42c to 45c arranged respectively on light incident surfaces of the optical sensors 42b to 45b, as shown in FIG. 3. In the present modified example, the light detection section is composed of the optical sensors 42b to 45b and the dimmer filters 42c to 45c.

Each of the dimmer filters 42c to 45c reduces the quantity of the light, which is emitted from each of the LEDs 42 to 45 to be incident on each of the optical sensors 42b to 45b, to one tenth or one hundredth of the original quantity, for example, with the filter characteristics. Therefore, if abnormality such as falling, failure, incapability of dimming or the like occurs in the dimmer filters 42c to 45c, the quantity of light to be incident on each of the optical sensors 42b to 45b becomes extremely larger than the predetermined light quantity.

When the detection result of any of the optical sensors 42b to 45b is extremely larger than the predetermined light quantity, the control section 41 is capable of detecting the detection result as the abnormality in the dimmer filters 42c to 45c, that is, the abnormality in the light detection section. When the control section 41 detects the abnormality in any of the dimmer filters 42c to 45c, since the LEDs 42 to 45 are normal, the control section 41 fixes the driving current values of the LED 42 to 45 respectively to the driving current values at which substantially white illumination light is obtained, controls the LED driving section 46 such that automatic light control is performed only with PWM control, to ensure minimum brightness necessary for observation.

On the other hand, when the detection result of any of the optical sensors 42b to 45b is smaller than the predetermined light quantity, the control section 41 detects the detection result as abnormality in the LEDs 42 to 45. When detecting the abnormality in the LEDs 42 to 45, the control section 41 stops the LED in which abnormality has been detected, controls the LED driving section 46 to fix the driving currents of the LEDs other than the LED in which abnormality has been detected, to ensure the minimum brightness necessary for the observation.

As described above, the light source apparatus 40a according to the modified example is capable of easily determining the member in which abnormality occurs depending on the detection results of the optical sensors 42b to 45b, in addition to the same effects as those in the first embodiment.

(Second Embodiment)

Next, the second embodiment will be described.

In the present embodiment, description will be made on a light source apparatus that is capable of discriminating the failure in the LEDs (or LED driving section) and the failure in the optical sensors, and performing error handling processing according to the state of the failure.

Figure 4:
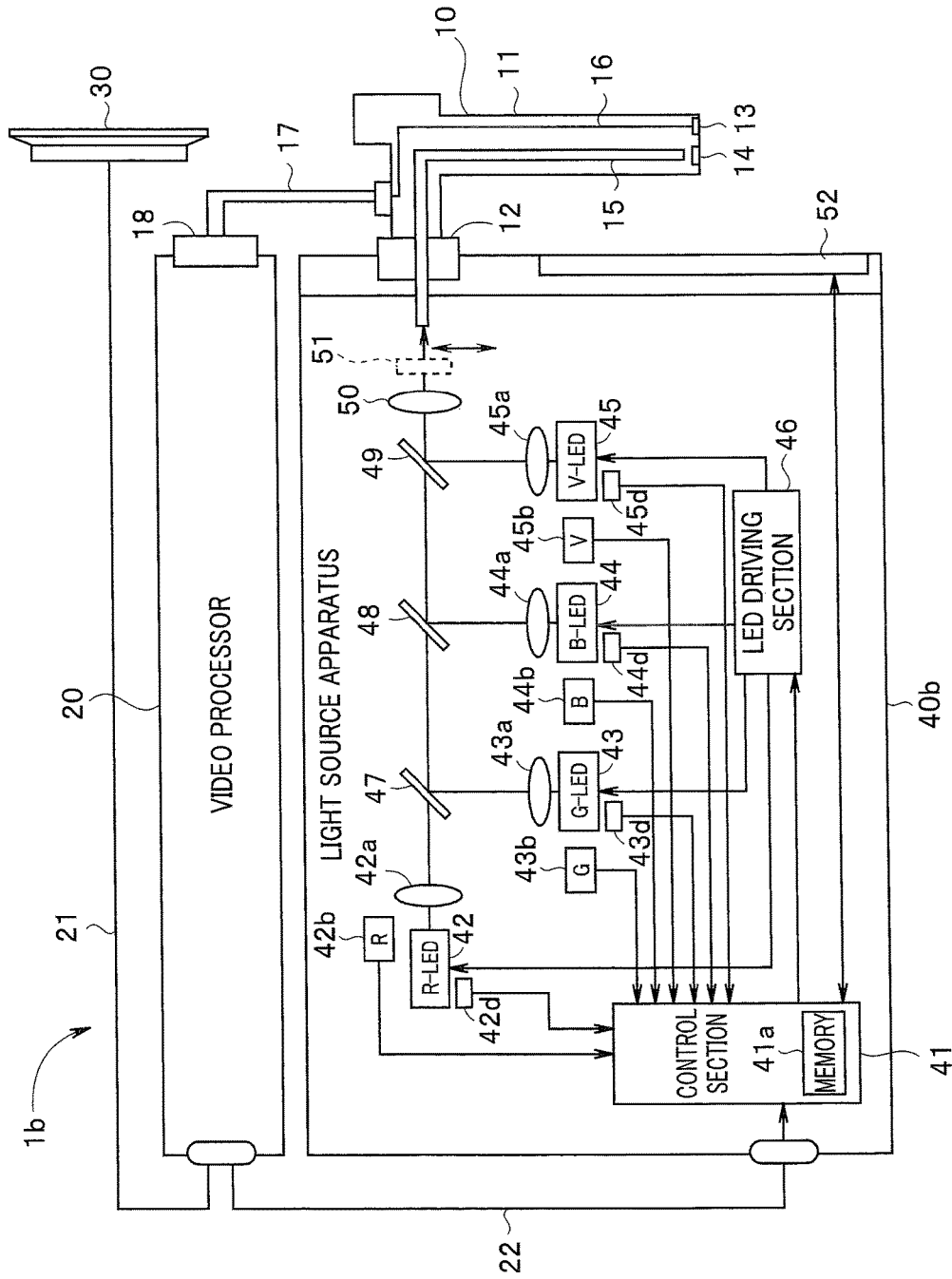
FIG. 4 is a block diagram showing a configuration of an endoscope system including a light source apparatus according to a second embodiment.

FIG. 4 is a block diagram showing a configuration of an endoscope system including a light source apparatus according to the second embodiment. Note that, in FIG. 4, the same constituent elements as those in FIG. 1 are attached with the same reference numerals and descriptions thereof will be omitted.

As shown in FIG. 4, a light source apparatus 40b is configured by additionally providing temperature sensors 42d to 45d that respectively detect the temperatures of the LEDs 42 to 45 in the light source apparatus 40 in FIG. 1. The temperature sensors 42d to 45d are arranged so as to be adjacent respectively to the LEDs 42 to 45, and configured to detect the temperatures of the LEDs 42 to 45 and output the detection results to the control section 41. Note that description will be made supposing that the temperature sensors 42d to 45d respectively detect the temperatures of the LEDs 42 to 45. However, the temperature sensors may be configured to detect the temperatures of the substrates on which the LEDs 42 to 45 are mounted, for example.

Figures 5A, 5B:
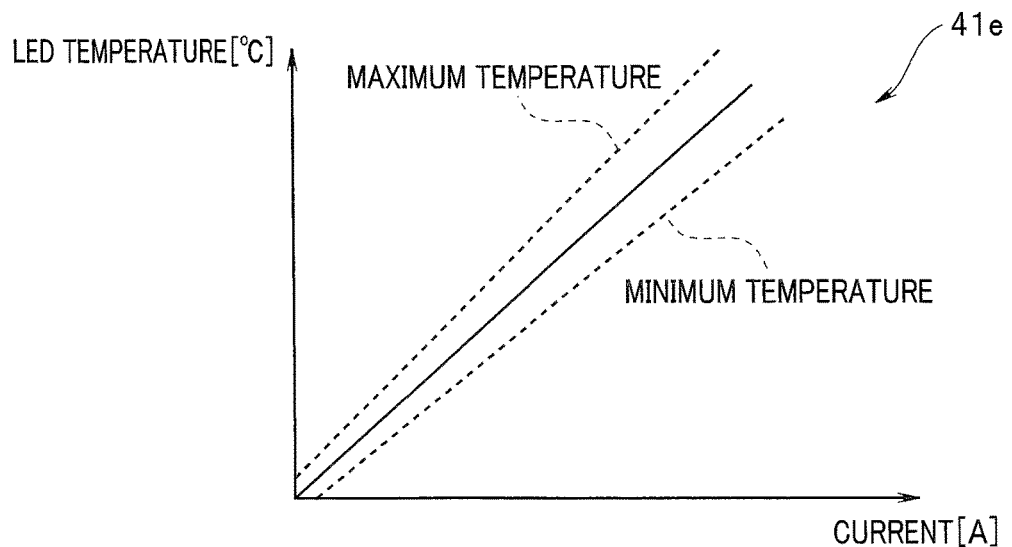

In the memory 41a of the control section 41, information indicating the relation between the driving currents and the temperatures of the LEDs as shown in FIGS. 5A and 5B is stored, in addition to the information shown in FIGS. 2A and 2B.

FIGS. 5A and 5B illustrate one example of the information stored in the memory 41a. In particular, FIG. 5A is a table for explaining one example of the information stored in the memory 41a, and FIG. 5B is a graph for explaining one example of the information stored in the memory 41a.

As shown in FIG. 5A, the correspondence relation among the driving currents, the minimum temperature values, and the maximum temperature values of the LEDs 42 to 45 is stored in the table 41d. Note that, if the relation among the driving currents, the minimum illuminance, and the maximum illuminance of the LEDs 42 to 45 is different in each of the LEDs 42 to 45, a table for each of the LEDs 42 to 45 may be stored in the memory 41a. In addition, the memory 41a may store the information of the graph 41e shown in FIG. 5B, instead of the table 41d in FIG. 5A.

First, the control section 41 determines whether or not the illuminance value of each of the LEDs 42 to 45 is within a predetermined range of illuminance values, based on the detection result of each of the optical sensors 42b to 45b. When the illuminance value of each of the LEDs 42 to 45 is within the predetermined range of illuminance values, the control section 41 determines that the LED 42 to 45, the optical sensors 42b to 45b, and the LED driving section 46 are normal. When the illuminance value of any of the LEDs 42 to 45 is not within the predetermined range of illuminance values, the control section 41 determines that abnormality occurs in the LEDs 42 to 45, the optical sensors 42b to 45b, or LED driving section 46.

Next, when determining that any of the detection results of the optical sensors 42b to 45b indicates abnormality, the control section 41 performs error determination based on the detection results of the temperature sensors 42d to 45d. The control section 41 determines whether or not the detection results of the temperature sensors 42d to 45d are within a predetermined range of temperatures.

When the detection results of the temperature sensors 42d to 45d are within the predetermined range of temperatures, the control section 41 determines that failure occurs in the optical sensors 42b to 45b, since the detection results of the light quantities are not normally acquired although the LEDs 42 to 45 are normally lighted on. When determining that failure occurs in the optical sensors 42b to 45b, the control section 41 ensures the field of view of the endoscope, with the driving currents of all of the LEDs 42 to 45 set to fixed values, since failure does not occur in the LEDs 42 to 45 themselves. As the current values at the time when the driving currents of all of the LEDs 42 to 45 are set to fixed values, the control section 41 sets, for the LEDs 42 to 45, expected current values at which substantially white illumination light is expected to be obtained. Note that the control section 41 may set only the driving current of the LED which is paired with the optical sensor determined as a failure optical sensor to a fixed value. In addition, even in the case where the driving currents are set to fixed values in the above-described two patterns, the control section 41 is capable of performing automatic light control through PWM control using the same pulse width for the LEDs 42 to 45. Since the same pulse width is used for all of the LEDs 42 to 45, light control is possible while maintaining the color state at the time when the current values are fixed.

When any of the detection results of the temperature sensors 42d to 45d is not within the predetermined range of temperatures, the control section 41 determines that failure occurs in any of the LEDs 42 to 45, as the correct lighting processing not being performed on the LEDs 42 to 45 in response to the lighting instruction from the LED driving section 46. Otherwise, the control section 41 determines that failure occurs in the LED driving section 46, as the lighting instruction from the LED driving section 46 not being correctly executed for the LEDs 42 to 45, although the LEDs 42 to 45 are normal.

When the LEDs 42 to 45 are in open failure, since no current flows through the LEDs 42 to 45, the temperatures of the LEDs are below the minimum temperature, and when the LEDs 42 to 45 are in short failure, since overcurrent flows through the LEDs 42 to 45, the temperatures are above the maximum temperature.

When determining that failure occurs in the LEDs 42 to 45, the control section 41 determines whether or not the light quantity of each of the LEDs 42 to 45 is larger than the predetermined light quantity. When determining that the light quantity of any of the LEDs 42 to 45 is equal to or smaller than the predetermined light quantity, the control section 41 stops the driving of the LED determined as a failure LED among the LEDs 42 to 45. When determining that the light quantity of any of the LEDs 42 to 45 is larger than the predetermined light quantity, the control section 41 inserts the mesh member 51 for light quantity adjustment (or NBI filter) into the optical path between the lens 50 and the light guide 15.

Figure 6:
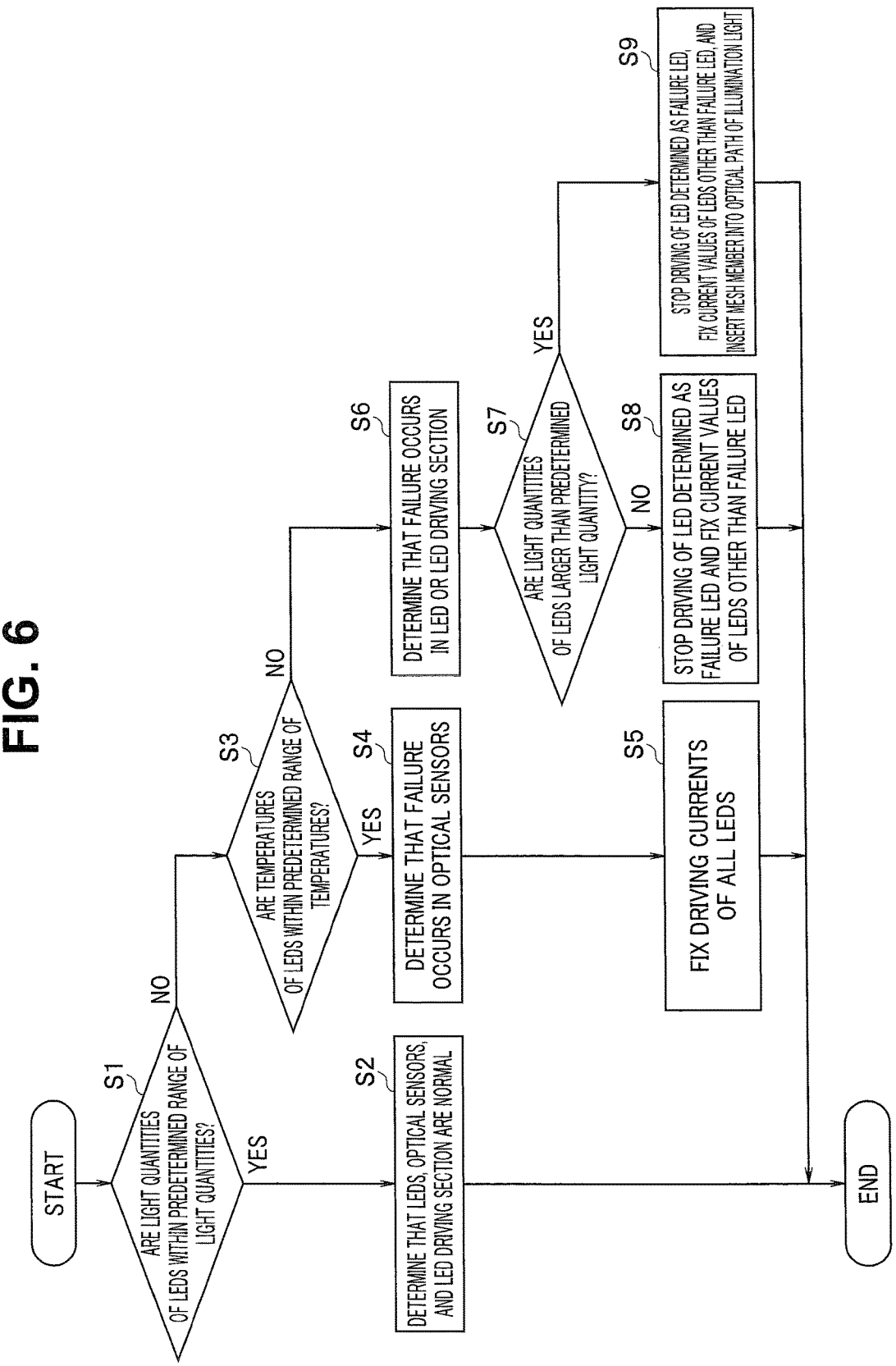
FIG. 6 is a flowchart for explaining an example of error-handling processing in a light source apparatus 40b.

Next, description will be made on the error handling processing in the light source apparatus 40b thus configured, with reference to FIG. 6. FIG. 6 is a flowchart for explaining the example of the flow of the error handling processing in the light source apparatus 40b.

First, the control section 41 determines whether or not the light quantity of each of the LEDs 42 to 45 is within the predetermined range of light quantities, based on the detection results of the optical sensors 42b to 45b (step S1). When determining that the light quantity of each of the LEDs 42 to 45 is within the predetermined range of light quantities, the procedure proceeds to YES and the control section 41 determines that the LED 42 to 45, the optical sensors 42b to 45b and the LED driving section 46 are normal (step S2), to terminate the processing.

When the control section 41 determines that the light quantity of any of the LEDs 42 to 45 is not within the predetermined range of light quantities, the procedure proceeds to No, and the control section 41 determines whether or not the temperature of each of the LEDs 42 to 45 is within a predetermined range of temperatures, based on the detection results of the temperature sensors 42d to 45d (step S3). When the control section 41 determines that the temperature of each of the LEDs 42 to 45 is within the predetermined range of temperatures, the procedure proceeds to YES, and the control section 41 determines that failure occurs in the optical sensors 42b to 45b (step S4). Then, the control section 41 controls the LED driving section 46 to fix the driving currents of all of the LEDs 42 to 45 (step S5), to terminate the processing.

When the control section 41 determines that any of the temperatures of the LEDs 42 to 45 is not within the predetermined range of temperatures, the procedure proceeds to NO, and the control section 41 determines that failure occurs in the LEDs 42 to 45 or in the LED driving section 46 (step S6). Next, the control section 41 determines whether or not the light quantity of each of the LEDs 42 to 45 is larger than the predetermined light quantity (step S7).

When the control section 41 determines that the light quantity of any of the LEDs 42 to 45 is equal to or smaller than the predetermined light quantity, the procedure proceeds to NO, and the control section 41 stops the driving of the LED determined as a failure LED among the LEDs 42 to 45, fixes the current values of the LEDs other than the failure LED (step S8), and then terminates the processing. When the control section 41 determines that the light quantity of any of the LEDs 42 to 45 is larger than the predetermined light quantity, the procedure proceeds to YES, and the control section 41 stops the driving of the LED determined as a failure LED, fixes the current values of the LEDs other than the failure LED, inserts the mesh member 51 into the optical path of the illumination light (step S9), and then terminates the processing.

As described above, when any of the light quantity detection results of the LEDs 42 to 45 detected by the optical sensors 42b to 45b indicates light quantity abnormality, the light source apparatus 40b according to the present embodiment is capable of discriminating the failure in the LEDs 42 to 45 and the failure in the optical sensors 42b to 45b (or the LED driving section 46) by monitoring the temperature states of the LEDs 42 to 45 by the temperature sensors 42d to 45d, and performing optimal error handling processing depending on the state of the failure.

The light source apparatus according to the present embodiment is capable of discriminating the failure in the LEDs (or LED driving section) and the failure in the optical sensors and performing optimal error handling processing depending on the state of the failure, in addition to the effects same as those in the first embodiment.

Note that a common light source apparatus is provided with temperature sensors provided adjacent to the LEDs, for feedback of cooling control. Therefore, if the detection results of the temperature sensors for feedback of cooling control are substituted for the detection results for failure detection in the present embodiment, there is no need for additionally providing temperature sensors in the light source apparatus according to the present embodiment.

Figure 7A:
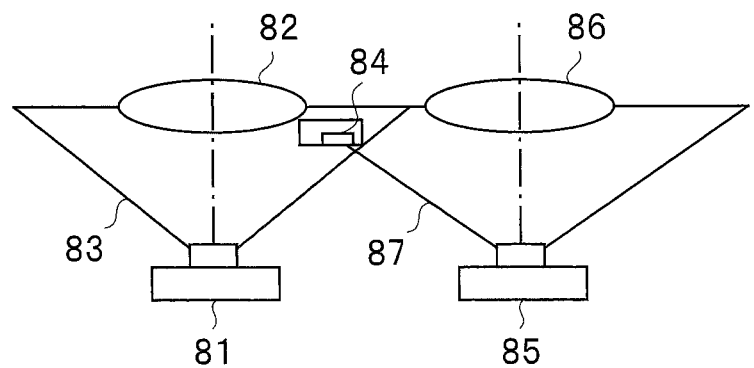
FIG. 7A illustrates an example of two LEDs 81 and 85 arranged close to each other.
Figure 7B:
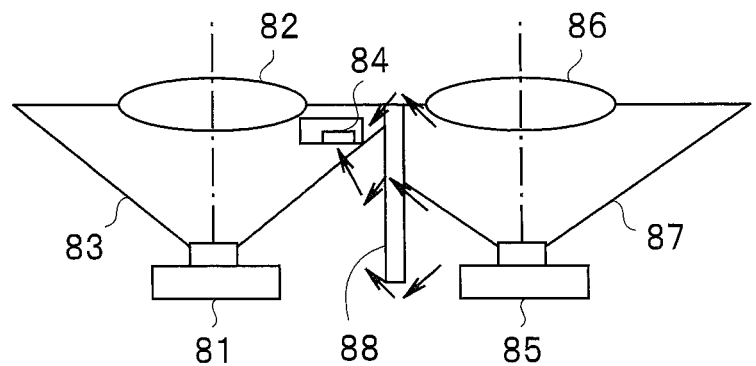
FIG. 7B illustrates an example of the two LEDs 81 and 85 arranged close to each other.

Incidentally, size reduction is required for the light source apparatus for endoscope. Therefore, the LEDs and the optical sensors are arranged so as to be close to each other. FIGS. 7A and 7B illustrate the two LEDs 81 and 85 arranged close to each other. The lenses 82 and 86 are arranged respectively on the optical paths of the LEDs 81 and 85. The lenses 82 and 86 respectively convert the light beams emitted from the LEDs 81 and 85 into substantially parallel light beams.

Optical sensors 84 that respectively detect the light quantities of the LEDs 81 and 85 are provided in ranges 83, 87 of the emitted light beams of the LEDs 81 and 85. Note that FIGS. 7A and 7B illustrate only the optical sensor 84 that detects the light quantity of the LED 81. The optical sensor 84 is arranged in the range 83 of the emitted light beam of the LED 81 and configured to detect the light of the LED 81. However, as shown in FIG. 7A, when the LEDs 81 and 85 are arranged close to each other, a part of emitted light beam from the LED 85 is also incident on the optical sensor 84. As a result, the optical sensor 84 cannot accurately detect the emitted light beam from the LED 81, which is likely to negatively affect the color balance of the LEDs 81 and 85.

FIG. 7B illustrates an example in which a shielding wall 88 is arranged between the LED 81 and the LED 85 to prevent the detection of leak light (ambient light) from the adjacent LED. However, in this case, the light from the LED 85 is incident on the optical sensor 84 from the gap of the shielding wall 88, as shown by the arrows in FIG. 7B.

When a plurality of LEDs and optical sensors are thus arranged in a relatively small range, it is very difficult for the respective optical sensors to accurately detect the light quantities of the respective LEDs as detection objects.

Therefore, description will be made on a light detection section that is capable of reducing the ratio of the ambient light to the light desired to be detected, with reference to FIGS. 8A, 8B, and 8C.

Figure 8A:
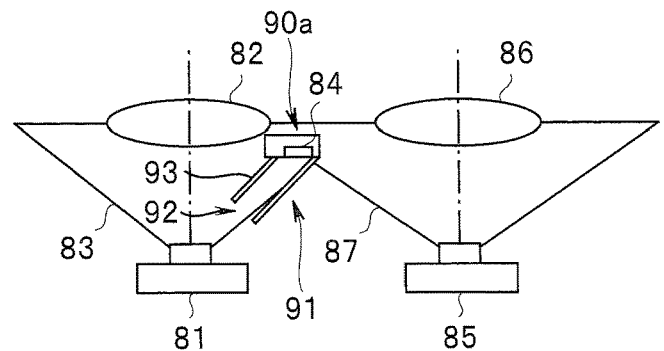
FIG. 8A is a view illustrating an exemplary configuration of a light detection section capable of reducing a ratio of ambient light to light desired to be detected.
Figure 8B:
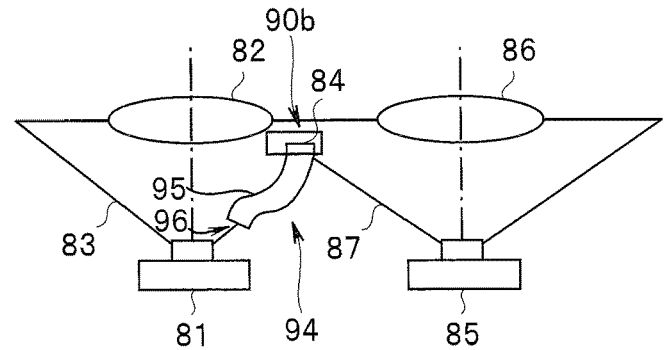
FIG. 8B is a view illustrating an exemplary configuration of the light detection section capable of reducing the ratio of ambient light to light desired to be detected.
Figure 8C:
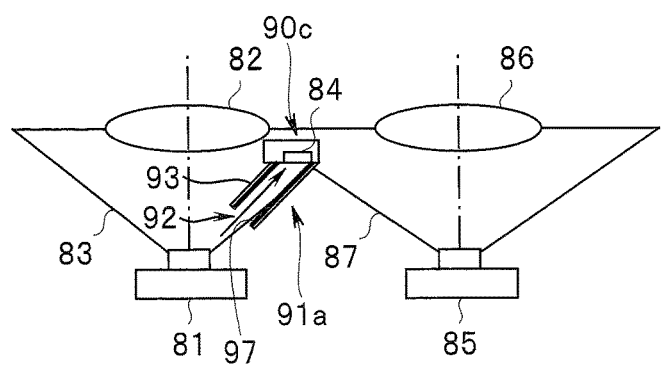
FIG. 8C is a view illustrating an exemplary configuration of the light detection section capable of reducing the ratio of ambient light to light desired to be detected.

FIGS. 8A, 8B, and 8C each illustrate an exemplary configuration of the light detection section that is capable of reducing the ratio of the ambient light to the light desired to be detected. As shown in FIG. 8A, a light detection section 90a includes a substantially cylindrical-shaped light-guiding member 91 provided so as to surround the optical sensor 84. The light-guiding member 91 includes a substantially circular-shaped incident portion 92, and a substantially cylindrical-shaped light-guiding portion 93.

The incident portion 92 is arranged so as to face in the direction of the LED 81 as a detection object. The light-guiding portion 93 has a predetermined length so as to prevent the direct light from the adjacent LED 85, which becomes ambient light, from being incident on the incident portion 92.

Such a configuration enables the direct light from the LED 85 which is not desired to be detected to be shielded, and enables the light from the LED 81 which is desired to be detected to be mainly incident on the optical sensor 84. As a result, the light detection section 90a is capable of reducing the intensity ratio of the ambient light to the light from the LED 81 which is desired to be detected. Therefore, the light source apparatus including such a light detection section 90a is capable of ensuring the color balance between the LED 81 and the LED 85 (light emission ratio of the LEDs of respective colors), and providing an optimal endoscopic image.

In addition, a light detection section 90b in FIG. 8B includes an optical fiber 94 constituted of a substantially circular-shaped incident portion 95 and a substantially cylindrical-shaped light-guiding portion 96, instead of the light-guiding member 91 in FIG. 8A. The incident portion 95 provided at the distal end of the optical fiber 94 is arranged so as to face in the direction of the LED 81 desired to be detected.

Since the incident portion 95 is thus arranged so as to face the LED 81 desired to be detected, even if the light from the LED 85 which is not desired to be detected is incident on the incident portion 95, the light from the LED 85 is incident on the incident portion 95 at an angle equal to or larger than a critical total reflection angle. In this case, the light from the LED 85 passes through from the exterior of the optical fiber 94 and is not guided to the optical sensor 84, and only the light from the LED 81, which is incident on the incident portion 95 at the angle smaller than the critical total reflection angle, is guided to the optical sensor 84.

As a result, the light detection section 90b enables the light from the LED 81 desired to be detected to be mainly incident on the optical sensor 84, similarly as the light detection section 90a in FIG. 8A. Therefore, also the light source apparatus including such a light detection section 90b is capable of ensuring the color balance between the LED 81 and the LED 85 and providing an optimal endoscopic image.

A light detection section 90c in FIG. 8C includes a light-guiding member 91a, instead of the light-guiding member 91 in FIG. 8A. The light-guiding member 91a has substantially the same configuration as that of the light-guiding member 91, and includes a substantially circular-shaped incident portion 92 and a substantially cylindrical-shaped light-guiding portion 93. The inner surface of the light-guiding portion 93 is a light absorbing surface 97.

Such a configuration allows only the direct light from the LED 81 desired to be detected (light which does not hit the light absorbing surface 97) to be incident on the optical sensor 84, as shown with the arrow in FIG. 8C. Even when the light from the LED 85 which is not desired to be detected is incident on the light-guiding member 91a, the light is absorbed by the light absorbing surface 97 and is not incident on the optical sensor 84.

As a result, the light detection section 90c enables the light from the LED 81 desired to be detected to be mainly incident on the optical sensor 84, similarly as the light detection section 90a in FIG. 8A. Also the light source apparatus including such a light detection section 90c is capable of ensuring the color balance between the LED 81 and the LED 85, and providing an optimal endoscopic image.

Note that execution order of the steps in the flowchart in the present description may be changed, a plurality of the steps may be simultaneously executed, or may be executed in a different order for each execution, unless contrary to the gist of the invention.

The present invention is not limited to the above-described embodiments, and various changes and modifications are possible in a range without changing the gist of the present invention.

What is claimed is:

1. A light source apparatus for an endoscope, the light source apparatus comprising:
    a first light source configured to emit first illumination light;
    a second light source configured to emit second illumination light, wherein a color of the second illumination light is different from a color of the first illumination light;
    a light source driver configured to be controlled to drive the first light source and the second light source;
    a first light detection sensor configured to detect brightness of the first illumination light emitted from the first light source;
    a second light detection sensor configured to detect brightness of the second illumination light emitted from the second light source,
        wherein the first light detection sensor is arranged relative to the first light source and the second light source such that the first illumination light is mainly incident on the first light detection sensor relative to the second illumination light;
    a first temperature detection sensor configured to detect a temperature of the first light source; and
    a controller configured to:
        determine whether or not the brightness of the first illumination light detected by the first light detection sensor is within a range of brightness of the first illumination light capable of being emitted from the first light source under a normal condition of the first light source, wherein the brightness corresponds to a driving current for driving the first light source;
        in response to determining that the brightness of the first illumination light detected by the first light detection sensor is outside the range of brightness, determine whether or not the temperature of the first light source detected by the first temperature detection sensor is within a range of temperature of the first light source under the normal condition of the first light source, wherein the temperature corresponds to the driving current for driving the first light source;
        in response to determining that the brightness of the first illumination light is outside the range of brightness and the temperature of the first light source is within the range of temperature, control the light source driver to set the driving current for driving the first light source and a driving current for driving the second light source to fixed values, as controlling for a case of abnormality in the first light detection sensor; and
        in response to determining that the brightness of the first illumination light is outside the range of brightness and the temperature of the first light source is outside the range of temperature, control the light source driver to stop the driving of the first light source and set the driving current for driving the second light source to a fixed value, as controlling for a case of abnormality in the first light source.

2. The light source apparatus according to claim 1, wherein the first light detection sensor comprises:
   a dimmer filter configured to dim the first illumination light emitted from the first light source,
   wherein the first light detection sensor is configured to detect brightness of the first illumination light dimmed by the dimmer filter.

3. The light source apparatus according to claim 1, further comprising:
   a guide configured to guide the first illumination light to be incident on the first light detection sensor and to shield the second illumination light from being incident on the first light detection sensor.

4. The light source apparatus according to claim 3, wherein the guide comprises a light guide having an incident end arranged to face in the direction of the first light source.

5. The light source apparatus according to claim 4, wherein the guide further comprises a light absorbing surface arranged to the light guide, wherein the light absorbing surface is configured to perform one or more of absorbing a portion of the first illumination light that is not directly incident on the first light detection sensor and absorbing a portion of the second illumination light that is incident on the light guide.

6. The light source apparatus according to claim 3, wherein the guide comprises an optical fiber having an incident end arranged to face in the direction of the first light source.

7. The light source apparatus according to claim 1, wherein the light source driver is configured to generate pulse signals as a driving signal for the first light source and a driving signal for the second light source, and
wherein the controller is configured to:
   control a duty ratio of the pulse signals generated by the light source driver and current levels of the pulse signals; and
   control the duty ratio, with a pulse width of the driving signals for the first light source being equal to a pulse width of the driving signals for the second light source, as controlling for the case of abnormality in the first light detection sensor.

* * * * *